United States Patent [19]

McCormack

[11] 4,087,749
[45] May 2, 1978

[54] METHOD AND APPARATUS FOR NORMALIZING THE OUTPUTS OF SEQUENTIALLY SCANNED MAGNETIC FLAW DETECTORS

[75] Inventor: Ray G. McCormack, St. Joseph, Ill.

[73] Assignee: The United States of America as represented by the Secretary of the Army, Washington, D.C.

[21] Appl. No.: 762,373

[22] Filed: Jan. 25, 1977

[51] Int. Cl.² .......................................... G01R 33/12
[52] U.S. Cl. .................................. 324/225; 324/235; 324/263
[58] Field of Search ............................ 324/37, 40, 45

[56] References Cited

U.S. PATENT DOCUMENTS

| | | | |
|---|---|---|---|
| 1,933,547 | 11/1933 | Drake et al. | 324/37 |
| 1,998,952 | 4/1935 | Edgar et al. | 324/45 |
| 2,295,382 | 9/1942 | Brace | 324/37 |
| 2,770,773 | 11/1956 | Cooley | 324/37 |
| 3,015,063 | 12/1961 | Ownby | 324/37 |
| 3,247,453 | 4/1966 | Quittner | 324/37 |
| 3,284,701 | 11/1966 | Kerbow | 324/37 |
| 3,529,236 | 9/1970 | Proctor | 324/37 |

FOREIGN PATENT DOCUMENTS 950,696  2/1964  United Kingdom .................. 324/37

Primary Examiner—Robert J. Corcoran
Attorney, Agent, or Firm—Thomas O. Maser

[57] ABSTRACT

A method and apparatus for detecting flaws in conduits or the like which comprises positioning an annular array of Hall-effect devices transversely around the conduit, applying an electric current to the conduit to flow longitudinally therethrough so as to create a magnetic field around the conduit, sequentially scanning the Hall-effect devices to produce a series of output signals corresponding to the portions of the magnetic field sensed respectively by them, and comparing the output signals for nonuniformities among them, the nonuniformities being indicative of the existence and location of flaws.

5 Claims, 6 Drawing Figures

METHOD AND APPARATUS FOR NORMALIZING THE OUTPUTS OF SEQUENTIALLY SCANNED MAGNETIC FLAW DETECTORS

BACKGROUND OF THE INVENTION

The present invention relates to a method and apparatus for non-destructively testing steel or other metal conduits to determine the existence and location of flaws.

In a great many applications, it is desirable to be able to examine a metal conduit for flaws or other imperfections which may not be visible to the eye either because of their size or because they are located on the interior wall of the conduit and therefore cannot be seen without internal examination. Non-destructive testing of pipes or conduits is also advantageous to determine if couplings or fittings are seated properly. For example, when assembling a conduit system for use in electromagnetic pulse hardening of electrical, electronic or communications wiring and cabling, it is necessary to determine if couplings are properly tightened and provide good shielding.

One class of apparatus for detecting flaws in metal objects comprises impressing on the object an alternating magnetic field which induces eddy currents which in turn produce their own magnetic fields. The presence of faults or irregularities in the object cause asymmetry or nonuniformity in the eddy current created magnetic fields which can be detected by means of suitable magnetic detectors such as Hall-effect devices. In U.S. Pat. No. 3,944,911 to Tornblom, the induced field rotates about the axis of the conduit and asymmetry in the detected magnetic field indicates a fault.

In a number of the prior art devices, a single magnetic sensor is utilized and must be moved over the surface of the object to detect and locate any faults which might be present. Alternatively, the conduit could be rotated past a stationary sensor. Such relative rotation between the magnetic field sensor and conduit creates a number of problems, however, especially when it is not possible to rotate the conduit. If the sensor must be rotated, electrical brushes or the like are required to provide contact between it and electrical processing apparatus. Furthermore, rather complicated mechanical drive mechanisms would be required to rotate the detector sensor in an arcuate path around the conduit. It is also necessary to assure that the path followed by the sensor is concentric with the conduit since the intensity of the magnetic field is often a function of distance from the conduit in a radial direction.

Although prior art devices are known which comprise a plurality of magnetic sensors positioned in a circular array within or outside a conduit for the purpose of flaw or joint detection, processing of the signals from the individual detectors is often complex and inprecise as to the exact location of the flaw. U.S. Pat. No. 3,166,710 to Schmidt and U.S. Pat. No. 3,843,923 to deVries et al are examples of conduit testers employing a static array of magnetic sensors.

OBJECTS OF THE INVENTION

It is an object of the present invention to provide a method and apparatus for detecting flaws in conduits which requires no relative rotation between the sensors and conduit.

Another object of the present invention is to provide a method and apparatus for detecting flaws in conduits where access cannot be secured to the interior of the conduit.

Another object of the present invention is to provide a method and apparatus for quickly and accurately locating flaws in conduits and determining whether conduit couplings are properly tightened.

A further object of the present invention is to provide a method and apparatus for non-destructively detecting and locating flaws in conduits where the exciting current can be either a direct or alternating current.

A still further object of the present invention is to provide a method and apparatus for detecting flaws in conduits whereby differences in the characteristics of the magnetic sensors are easily compensated for.

Yet another object of the present invention is to provide a method and apparatus for detecting flaws in conduits where all flaws will be detected regardless of their relative magnitudes.

A still further object of the present invention is to provide a method and apparatus for detecting flaws in conduits wherein the magnitude and location of flaws is graphically displayed.

SUMMARY OF THE INVENTION

A method for detecting flaws in elongated objects such as conduits or the like comprising: positioning an annular array of discrete magnetic field sensing devices transversly around the object, applying an electric current to the object to flow longitudinally therethrough so as to create a magnetic field around the object, sequentially scanning the magnetic field sensing devices to produce a series of output signals corresponding to the magnetic fields sensed respectively by the devices, and comparing the output signals for non-uniformities among them, the non-uniformities being indicative of flaws.

Apparatus for detecting flaws in conduits or the like comprising means for applying electric current to the conduit so as to create a magnetic field around the conduit, a circular array of discrete magnetic sensor means responsive to the presence of a magnetic field to provide an output signal related to the sensed magnetic field, said array being adapted to be positioned around the conduit, means operatively connected to the sensor means for sequentially scanning the output signals, and means for comparing the output signals to detect non-uniformities among them relative to each other, said non-uniformities being indicative of flaws.

DETAILED DESCRIPTION

Figure 1:
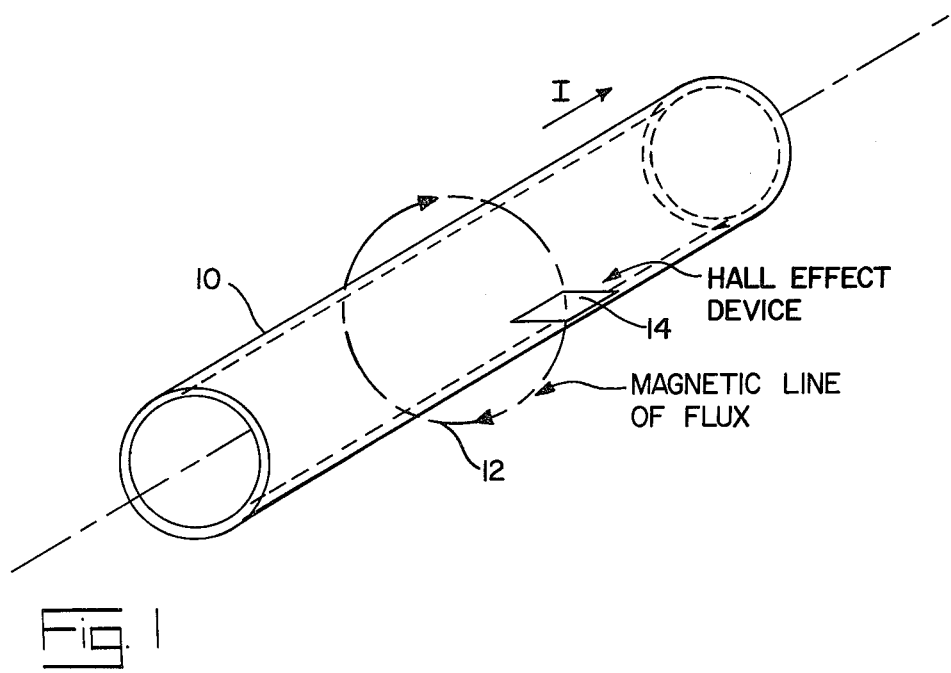
FIGS. 1 and 2 are schematic diagrams illustrating the electromagnetic principles underlying the present invention.
Figure 2:
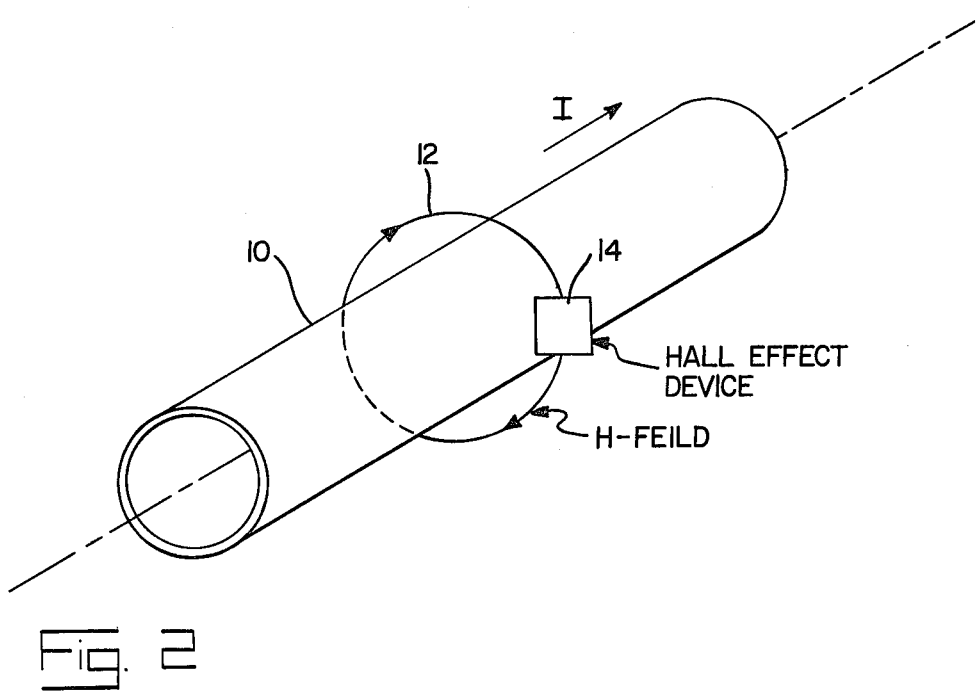

In basic terms, the invention comprises positioning a plurality of Hall-effect devices in a ring around a conduit and then applying a current to the conduit which preferably flows in a longitudinal direction with respect to its axis. As is well-known, when an electrical current flows in a uniform metallic cylinder, a uniform magnetic field is created around the cylinder with the lines of flux following a circular path concentric with the axis of the cylinder. This phenomenon is illustrated in FIGS. 1 and 2 where a current I flowing through the conduit 10 produces magnetic lines of flux such as 12. Although only a single line of flux is illustrated, the magnetic field extends outward from the surface of the conduit 10 along the entire length of the conduit 10 through which current is flowing. The intensity of the magnetic field decreases as the distance radially outward from the surface of the conduit 10 increases.

If the cylinder has a flaw, however, the density of the electric current in the immediate vicinity of the flaw is non-uniform so that not all current flows in a direction parallel to the axis of the cylinder 10. In accordance with well-known principles of electromagnetism, the direction of the lines of magnetic flux are dependent on the direction of current flow so that non-uniform current flow will produce irregularities in the magnetic field around the cylinder. This will result in some of the magnetic flux lines following paths which are not concentric to the axis of the cylinder 10, as is flux line 12.

An effective device for measuring not only the intensity but also the direction of magnetic flux is a Hall-effect device. This is a block of conducting material, usually a thin rectangular sheet, which, when placed in a magnetic field with its plane perpendicular to the field and electric current is applied longitudinally through the block, develops a potential difference across the block at right angles to the current flow and to the magnetic field. If the magnetic field flux is not perpendicular to the device, then the developed voltage is proportional to the normal component of the field. In this way, a Hall-effect device can be utilized to very accurately measure the orientation and intensity of the magnetic field.

In FIG. 1, the Hall-effect device 14 is shown oriented perpendicularly to the magnetic lines of flux so that the voltage developed is at a maximum. In FIG. 2, the Hall-effect device 14 is oriented parallel to the magnetic field so that the normal component of the field is zero thereby in a Hall voltage which is also zero. By moving the Hall-effect device in a circle centering on the axis of cylinder 10 and with a uniform orientation, the magnetic field around the conduit periphery may be measured. Both changes in intensity and direction will result in a change in the normal component of the field with respect to the Hall-effect device 14, which change will be reflected in the developed Hall voltage. If the Hall-effect device is kept parallel with the cross-sectional plane of the conduit as in FIG. 2 and the conduit current is maintained at a uniform value, the Hall-effect device 14 will have no output. If a conduit flaw such as a crack is present, however, the non-parallel conduit currents at that location as well as the induced magnetic field will be distorted thereby resulting in magnetic field components normal to the Hall-effect device 14 which in turn cause a voltage output to be produced.

Of course, the Hall-effect device 14 could be orientated in any direction so long as this orientation is maintained uniform with respect to the axis of the cylinder 10. It is also important to maintain the distance from the outer surface of the conduit 10 constant. The exact location of the flaw is easily determined by noting the position of the Hall-effect device both with respect to its axial and circumferential position.

Figure 3:
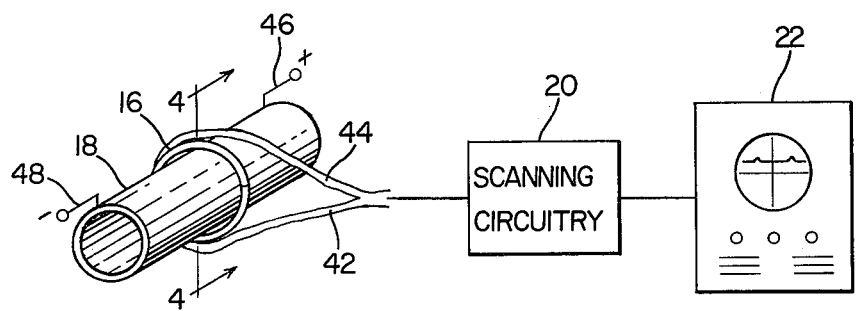
FIG. 3 is a perspective view of the Hall-effect probe clamped around a conduit and diagramatic representations of the scanning circuitry and display forming the primary components of the present invention.
Figure 4:
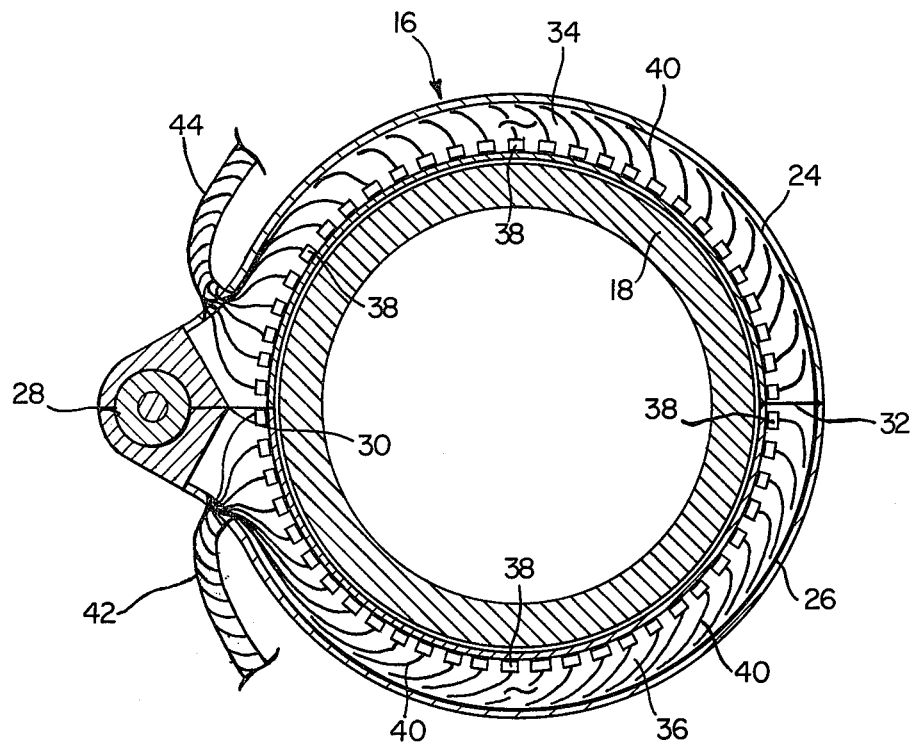
FIG. 4 is a sectional view of FIG. 3 taken along line 4—4 and viewed in the direction of the arrows.

Rather than rotating the Hall-effect device in a circular path around the conduit, the present invention contemplates providing a plurality of Hall-effect devices in a circular array around the conduit which are sequentially scanned to detect asymmetries in the induced magnetic field. Suitable apparatus for accomplishing this is illustrated in FIGS. 3 and 4. The apparatus comprises a Hall-effect probe 16 which is clamped around the conduit 18 and electrically connected to appropriate scanning circuitry 20 and an oscilliscope display 22. The probe 16 comprises an annular housing having two portions 24 and 26 hingedly connected at 28 and having mating surfaces at 30 and 32. By this arrangement, the probe 16 can be opened and clamped around the conduit 18. There is sufficient clearance between probe 16 and conduit 18 to permit probe 16 to be slid along it in the longitudinal direction. Portions 24 and 26 of probe 16 include channels 34 and 36 in which a plurality of Hall-effect devices 38 are mounted in a circular array concentric with the center of probe 16. As mentioned previously, it is important that the orientation of the Hall-effect devices be uniform with respect to this axis. The number of Hall-effect devices employed depends on the defect size of interest with greater resolution in detecting and locating the flaw being achieved with a larger number of Hall-effect devices.

Each Hall-effect device 38 requires a base current which can be provided by a single pair of wires to supply all devices 38. Output from the devices is transmitted to the scanning circuitry 22 either by means of a separate pair of wires for each device 38 or one wire from each device with a common grounding wire connected to all devices. These wires are shown at 40 which are bundled to form a pair of cables 42 and 44.

Longitudinal current is applied to conduit 18 by means of suitable connections illustrated schematically at 46 and 48. The current flowing in the conduit can be either alternating (AC) or direct (DC), but the use of DC current is preferred since AC requires more complex electronic circuitry for processing the output signals from the Hall-effect devices 38. Orientation of the Hall-effect devices is selected for maximum sensitivity to magnetic field disturbances of the type which are expected to be encountered.

As mentioned above, the outputs from the individual Hall-effect devices 38 are carried over cables 42 and 44 to the scanning circuitry 20 which sequentially samples the outputs and feeds them to oscilloscope 22.

Figure 5:
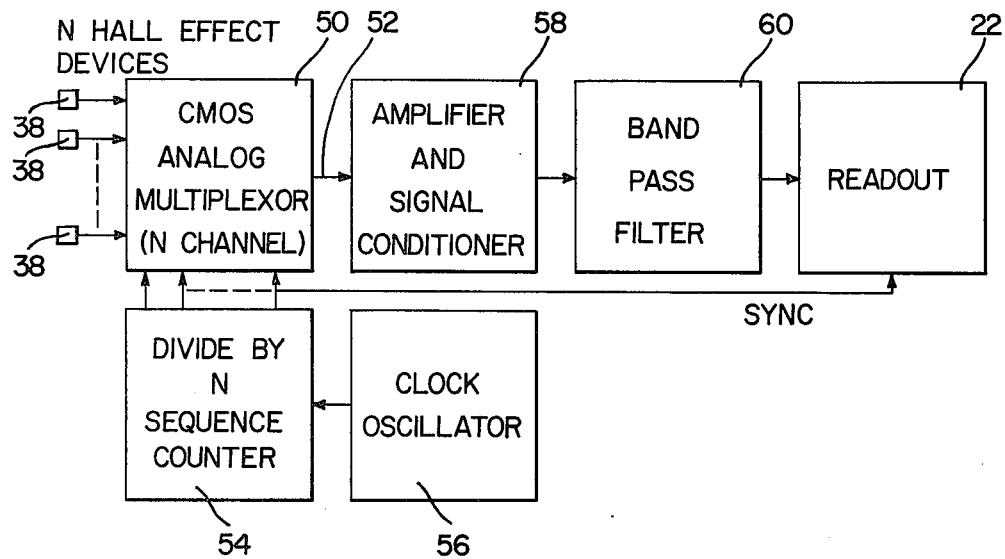
FIG. 5 is a block diagram of the signal processing circuitry for one embodiment of the present invention.

A block diagram of an appropriate circuit for accomplishing the sequential sampling and comparison is shown in FIG. 5. the outputs from the Hall-effect devices 38 are connected to a complimentary metal oxide semiconductor (CMOS) analog multiplexer 50 which may be in integrated circuit form and which utilizes CMOS transistors to switch a selected input 52. The input selected depends on a parallel code input which is derived from binary counter 54. Counter 54 is driven by clock oscillator 56 and sequences from zero through N, the number of Hall-effect devices 38 employed. By this arrangement, the output line shown schematically at 52 of multiplexer 50 is the sequentially sampled output from the N Hall-effect devices 38.

The outputs from the Hall-effect devices 38 are at a relatively low level and an amplifier and signal conditioner 58 brings the signals up to a level suitable for readout. A bandpass filter 60 filters out switching noise and removes the DC component of the signal. Any remaining AC signal component is then related to the H-field distortion around the conduit 18. A suitable display for graphically representing both the magnitude and position of the flaw is an oscilloscope 22 with its horizontal trace synchronized to the sequential scanning rate. By synchronizing the oscilloscope in this manner, the horizontal position on the trace of an irregularity representing a flaw is directly related to its angular position on the conduit. This enables flaw detection to be related to specific probe orientation. If no flaw were detected, the oscilliscope trace would be substantially straight.

Figure 6:
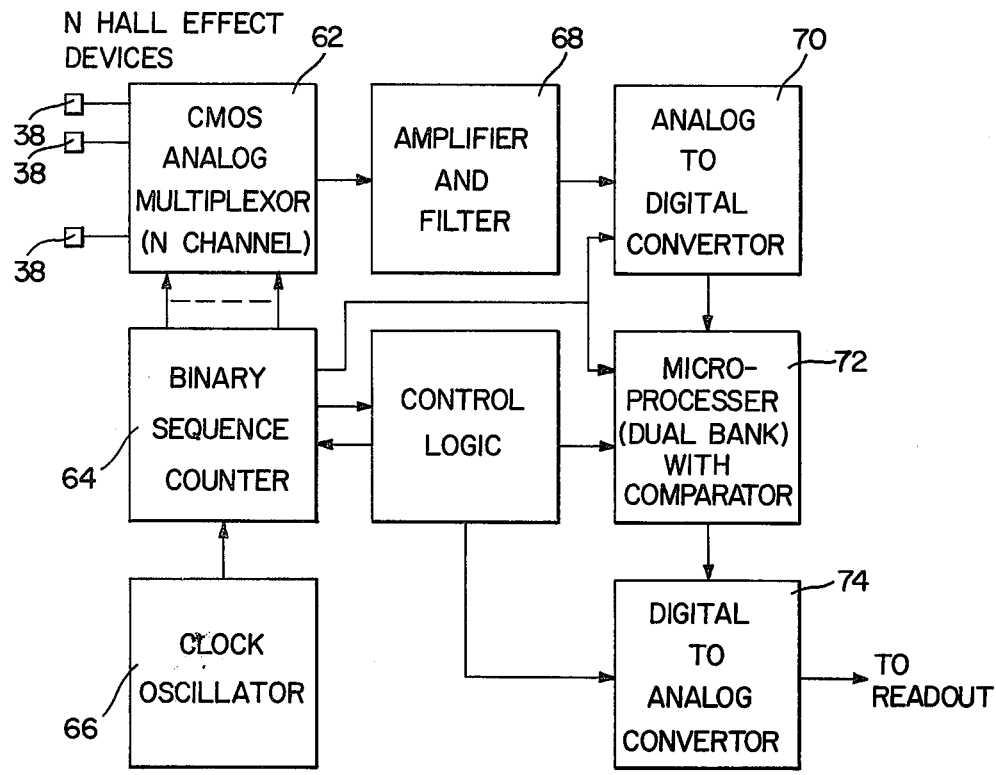
FIG. 6 is a block diagram of the signal processing circuitry of a further embodiment of the present invention.

FIG. 6 illustrates a further embodiment of the invention wherein means are provided to automatically compensate for using non-matched Hall-effect devices. This is accomplished by first clamping the probe 16 around a conduit which is known to be uniform and carrying a current equal to the standard test current. The output signals generated by the Hall-effect devices 38 are again sampled by an analog multiplexer 62, which is sequenced by counter 64 and clock oscillator 66. The sequentially sampled outputs are amplified and filtered at 68, converted to digital signals by A/D converter 70 and then stored in one memory bank of microprocessor 72.

Probe 16 is then placed around the conduit to be tested and sequential scanning again performed. The new digitally converted signals are then compared with the stored digital signals in a synchronized manner in microprocessor 72 such that the sample stored for each Hall-effect device 38 when taking reference data around the flawless conduit is compared with the new sample taken from the same probe 16 for the test conduit. Sequencing on the test conduit is then synchronized with the resequenced stored data for all Hall-effect devices 38. The digital output of the comparator in microprocessor 72 is converted to an analog signal in D/A converter 74 and subsequentially displayed on an oscilliscope. As was the case in the previous embodiment, deviations from a flat oscilloscope trace indicate flaws in the conduit. This embodiment enables the outputs from the Hall-effect devices 38 to in a sense be "normalized" thereby compensating for any mismatch between them.

By normalizing the Hall-effect device outputs, even conduits of non-circular configuration can be inspected. The differences in field intensity would be compensated by the stored standard values so that only flaw produced asymmetries around the conduit would produce non-uniformities in the oscilloscope trace.

While this invention has been described as having a preferred design, it will be understood that it is capable of further modification. The application is therefore intended to cover any variations, uses or adaptations of the invention following the general principles thereof and including such departures from the present disclosure as come within known or customary practice in the art to which this invention pertains, and as may be applied to the essential features hereinbefore set forth and fall within the scope of this invention or the limits of the claims.

What is claimed is:

1. A method for detecting flaws in elongated objects such as conduits or the like comprising:

positioning an annular array of discrete magnetic field sensing devices transversely around a standard object which is known to have no flaws, applying an electric current to the first object to flow longitudinally therethrough so as to create a magnetic field around the object, sequentially scanning the magnetic field sensing devices to produce a first series of output signals corresponding to the magnetic fields sensed respectively by the devices, storing the first series of output signals, positioning the circular array transversely around the elongated object which is to be tested, applying an electric current to the elongated object to be tested to flow longitudinally therethrough so as to create a magnetic field around it, sequentially scanning the magnetic field sensing devices to produce a second series of output signals corresponding to the magnetic fields sensed respectively by the devices, comparing said first and second series of output signals in a comparator to normalize said second series of signals, and comparing the normalized output signals of said second series for non-uniformities among them, the non-uniformities being indicative of flaws.

2. The method of claim 1 wherein:

the first series of output signals are stored in digital form, and the second series of signals are converted to digital form prior to comparison with the first series.

3. The method of claim 2 wherein the series of normalized signals are converted to analog form.

4. The method of claim 3 wherein the normalized signals are displayed on a scanning cathode ray tube in synchronism with the scanning of the respective magnetic field sensing devices.

5. Apparatus for detecting flaws in conduits or the like comprising:

means for applying electric current to the conduit so as to create a magnetic field around the conduit, an annular array of discrete magnetic sensor means positioned around the conduit and responsive to the presence of a magnetic field to provide a plurality of output signals related to the sensed magnetic field, means operatively connected to said sensor means for sequentially scanning said output signals, and processing means operatively connected to said scanning means comprising means for storing a predetermined standard value for each sensor, means for comparing each of said output signals with its respective standard value, means for adjusting each of said output signals to compensate for its respective standard value, and means for comparing said adjusted output signals to detect non-uniformities among them relative to each other, said non-uniformities being indicative of flaws.

* * * * *